(12) United States Patent
Kroll et al.

(10) Patent No.: US 8,099,174 B1
(45) Date of Patent: Jan. 17, 2012

(54) LEFT HEART IMPLANTABLE CARDIAC STIMULATION SYSTEM WITH CLOT PREVENTION ELECTRODE BODY COATING AND METHOD

(75) Inventors: Mark W. Kroll, Orono, MN (US); Josh Reiss, Bellevue, WA (US)

(73) Assignee: Pacesetter, Inc., Sylmark, CA (US)

( * ) Notice: Subject to any disclaimer, the term of this patent is extended or adjusted under 35 U.S.C. 154(b) by 922 days.

(21) Appl. No.: 11/361,338

(22) Filed: Feb. 23, 2006

Related U.S. Application Data

(63) Continuation-in-part of application No. 10/794,531, filed on Mar. 5, 2004, now Pat. No. 7,526,336.

(51) Int. Cl.
*A61N 1/08* (2006.01)

(52) U.S. Cl. .......................................... 607/121; 607/28

(58) Field of Classification Search ................ 607/121, 607/28
See application file for complete search history.

(56) References Cited

U.S. PATENT DOCUMENTS

| | | | |
|---|---|---|---|
| 3,512,183 A | 5/1970 | Sharp et al. | |
| 4,033,357 A | 7/1977 | Helland et al. | 128/418 |
| 4,265,928 A | 5/1981 | Braun | 427/2 |
| 4,280,514 A | 7/1981 | MacGregor | |
| 4,281,668 A | 8/1981 | Richter et al. | 128/784 |
| 4,506,680 A | 3/1985 | Stokes | |
| 4,711,251 A | 12/1987 | Stokes | |
| 4,745,923 A | 5/1988 | Winstrom | |
| 4,991,583 A | 2/1991 | Silvian | |
| 5,348,553 A | 9/1994 | Whitney | 606/41 |
| 5,496,360 A | 3/1996 | Hoffmann et al. | |
| 5,603,731 A | 2/1997 | Whitney | 607/121 |
| 5,713,944 A | 2/1998 | Kroll | |
| 5,713,945 A | 2/1998 | Fischer et al. | |
| 5,902,329 A | 5/1999 | Hoffmann et al. | |
| 6,010,573 A | 1/2000 | Bowlin | 118/620 |
| 6,317,615 B1 | 11/2001 | KenKnight et al. | 600/372 |
| 6,564,107 B1 | 5/2003 | Bodner et al. | 607/122 |
| 6,648,881 B2 | 11/2003 | KenKnight et al. | 606/32 |
| 6,810,286 B2 * | 10/2004 | Donovan et al. | 607/2 |
| 6,980,865 B1 | 12/2005 | Wang et al. | |
| 7,526,336 B2 | 4/2009 | Kroll | |
| 2002/0147470 A1 | 10/2002 | Weiner et al. | 607/9 |
| 2002/0169480 A1 * | 11/2002 | Zhu et al. | 607/2 |
| 2003/0130701 A1 | 7/2003 | Miller | 607/9 |
| 2003/0208236 A1 * | 11/2003 | Heil et al. | 607/3 |
| 2004/0098055 A1 | 5/2004 | Kroll et al. | |
| 2005/0021134 A1 | 1/2005 | Opie | |

FOREIGN PATENT DOCUMENTS

| | | |
|---|---|---|
| EP | 1 424 095 A1 | 6/2004 |
| WO | WO 99/21613 | 5/1999 |
| WO | WO 99/36193 | 7/1999 |

OTHER PUBLICATIONS

NonFinal Office Action, mailed Jul. 12, 2005: Related U.S. Appl. No. 10/794,531.

Final Office Action, mailed Nov. 23, 2005: Related U.S. Appl. No. 10/794,531.

(Continued)

*Primary Examiner* — Michael Kahelin

(57) ABSTRACT

An implantable cardiac stimulation device provides stimulation therapy from within the left ventricle of a heart. The device includes a pulse generator adapted to be coupled to an implantable cardiac stimulation electrode and a power supply that provides the stimulation electrode with a positive voltage. The positive voltage promotes coating of the electrode through a body coating process. The coating serves to repel formation of clots on the electrode.

8 Claims, 3 Drawing Sheets

OTHER PUBLICATIONS

Advisory Action, mailed Feb. 10, 2006: Related U.S. Appl. No. 10/794,531.
NonFinal Office Action, mailed Mar. 9, 2006: Related U.S. Appl. No. 10/794,531.
NonFinal Office Action, mailed Aug. 29, 2006: Related U.S. Appl. No. 10/794,531.
Final Office Action, mailed Mar. 19, 2007: Related U.S. Appl. No. 10/794,531.
Advisory Action, mailed May 15, 2007: Related U.S. Appl. No. 10/794,531.
NonFinal Office Action, mailed Aug. 14, 2007: Related U.S. Appl. No. 10/794,531.
Final Office Action, mailed Feb. 14, 2008—Related U.S. Appl. No. 10/794,531.
Advisory Action, mailed Apr. 22, 2008—Related U.S. Appl. No. 10/794,531.
Final Office Action, mailed Sep. 23, 2008—Related U.S. Appl. No. 10/794,531.
Advisory Action, mailed Dec. 5, 2008—Related U.S. Appl. No. 10/794,531.
Notice of Allowance, mailed Feb. 24, 2009—Related U.S. Appl. No. 10/794,531.
Restriction Requirement, mailed Dec. 15, 2009—Related U.S. Appl. No. 11/779,158.
NonFinal Office Action, mailed Feb. 22, 2010—Related U.S. Appl. No. 11/779,158.

* cited by examiner

LEFT HEART IMPLANTABLE CARDIAC STIMULATION SYSTEM WITH CLOT PREVENTION ELECTRODE BODY COATING AND METHOD

RELATED APPLICATION DATA

The present patent application is a continuation-in-part application of U.S. patent application Ser. No. 10/794,531, filed Mar. 5, 2004, now U.S. Pat. No. 7,526,336.

FIELD OF THE INVENTION

The present invention generally relates to an implantable cardiac stimulation system and more particularly to such a system for the left heart including at least one electrode having a clot formation preventive coating and method. The present invention is more particularly directed to such a system wherein at least one electrode is provided with a positive voltage after implant to cause the electrode to be coated by an accelerated body coating process. The resulting body coating opposes clot formation on the electrode.

BACKGROUND

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Notwithstanding the advancements in left heart therapy using leads/electrodes implanted in the coronary sinus region of the heart, it would still be very desirable to alternatively be able to place a lead/electrode in the left ventricular cavity. This would enable the electrode(s) to contact the left ventricular blood pool. Such blood pool contact would lower left heart pacing thresholds and hence extend device life by requiring lower pacing outputs. It would also enable more localized sensing of left heart activity and allow the ability to perform direct pressure, flow or other hemodynamic measurements. This would lead to better coordination of right heart side and left heart side therapy due to increased specificity in left heart activity detection.

As previously mentioned, direct access to the left heart, such as the left ventricle, has been limited due to the potential of clot formation around implanted leads and electrodes. The present invention addresses this issue by providing an implantable cardiac stimulation system capable of delivering stimulation pulses to an electrode implanted in the blood pool of the left ventricle while preventing clot formation which may be otherwise potentially occasioned by such an arrangement.

SUMMARY

What is described herein is an implantable cardiac stimulation device comprising a pulse generator adapted to be coupled to an implantable cardiac stimulation electrode and a power supply that provides the electrode with a voltage that induces an accelerated body coating process of the electrode. The electrode may be configured for implant in the left ventricle.

The voltage is a positive voltage. Preferably, the positive voltage is greater then 250 mV and less than two volts.

The device may further comprise a resistance monitor that monitors a resistance associated with the electrode and the power supply may maintain the voltage until the resistance reaches a certain value. The resistance monitor may measure an initial value of the resistance before the power supply provides the voltage and the certain resistance is preferably related to the initial resistance. The power supply may first provide the voltage at an initial level and then increase the voltage level until the resistance reaches the certain value.

In another embodiment, an implantable cardiac stimulation system comprises at least one implantable lead including at least one stimulation electrode and an implantable cardiac stimulation device comprising a pulse generator adapted to be coupled to the at least one stimulation electrode. The system further comprises a power supply that provides the electrode with a voltage that induces an accelerated body coating process of the electrode.

In yet another embodiment, a method comprises implanting an electrode in a chamber of a heart and applying a voltage to the electrode to cause the electrode to be coated through a body coating process. The voltage is preferably a positive voltage and the chamber is preferably a left ventricle of the heart.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1:
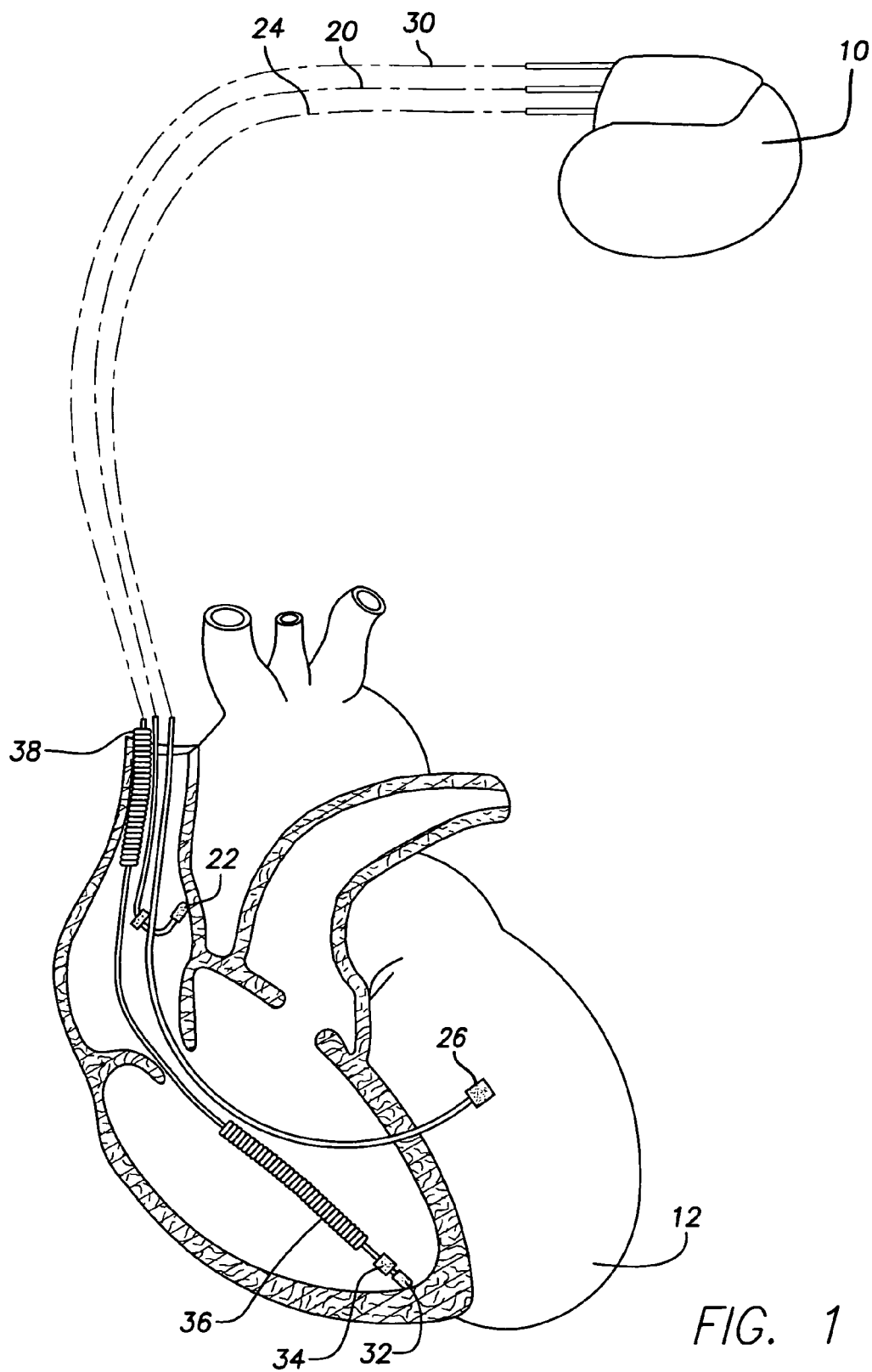
FIG. 1 is a simplified diagram illustrating an implantable stimulation device and lead system for delivering stimulation therapy to multiple chambers of a patient's heart including delivering pacing stimulation to the left ventricle.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left ventricular cardiac signals and to provide left ventricular pacing therapy, the stimulation device 10 is coupled to a lead 24 designed for placement in the left ventricle. The lead includes a left ventricular tip electrode 26 positioned in the blood pool of the left ventricle. To that end, the electrode 26 and lead 24 are fed down the superior vena cava (SVC), into the right atrium, into the right ventricle, and through the right ventricular septum into the left ventricle. Alternatively, but not shown, the electrode 26 and lead 24 may be fed into the right atrium, transseptally into the left atrium and then into the left ventricle as may be appreciate by those skilled in the art. As will be seen subsequently, the illustrative embodiment provides a means that prevents clot formation within the left ventricle which may otherwise potentially occur due to the presence of the lead 24 and electrode 26 within the left ventricle.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
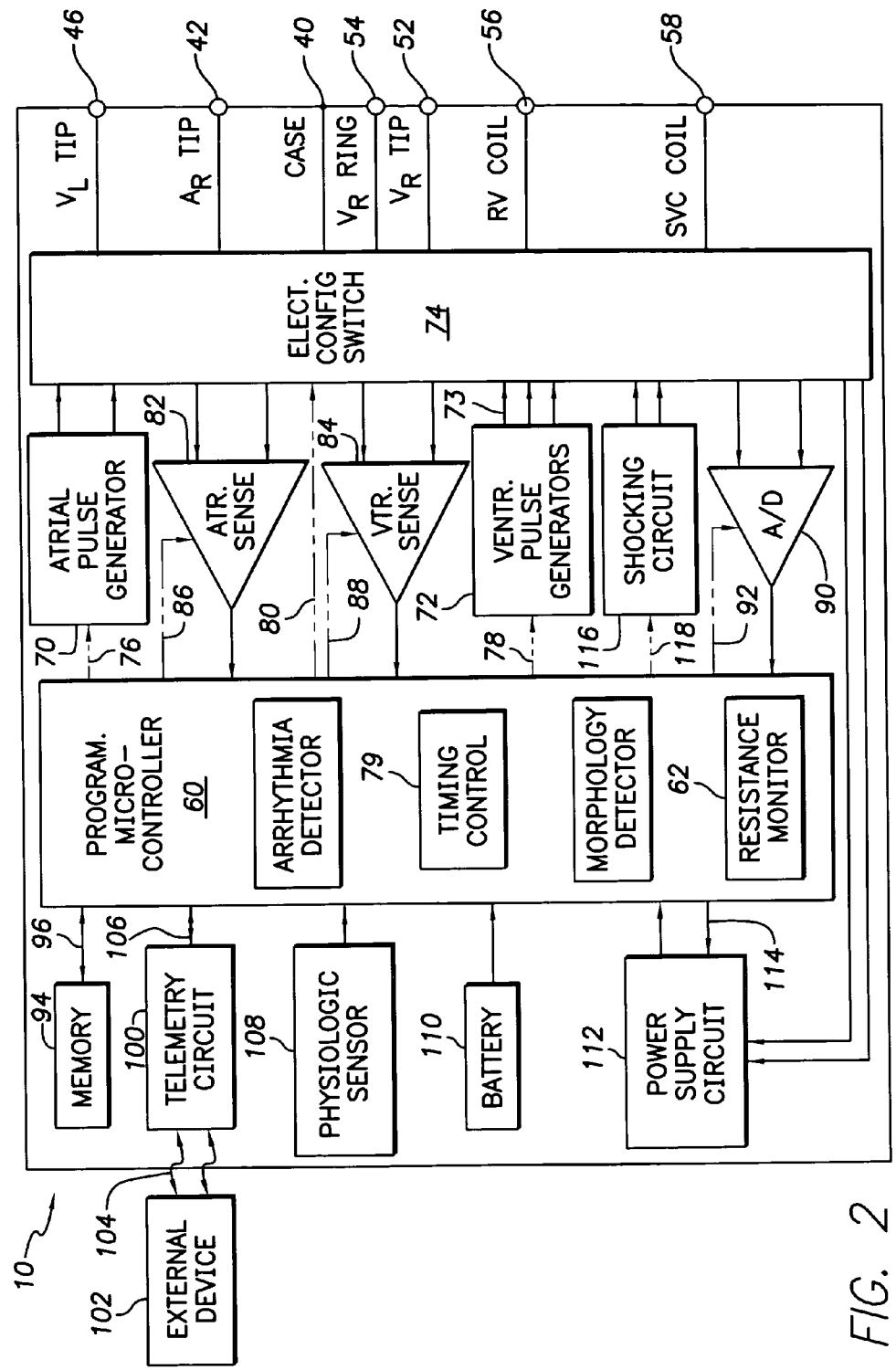
FIG. 2 is a functional block diagram of a multi-chamber implantable stimulation device according to one illustrative embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 46, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. To achieve left chamber sensing and pacing, the connector includes at least a left ventricular tip terminal ($V_L$ TIP) 46 adapted for connection to the left ventricular tip electrode 26. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and ventricular pulse generators 72 generate pacing stimulation pulses for delivery by the right atrial lead 20, the right ventricular lead 30, and/or the left ventricular coronary sinus lead 24 via an electrode configuration switch 74. The ventricular pulse generators 72 preferably include at least two dedicated, independent pulse generators. One pulse generator is preferably used to pace the right ventricle while the other pulse generator, to be described hereinafter with reference to FIG. 4, is particularly configured to provide pacing therapy to the left ventricle. The left ventricular pulse generator provides its pacing pulses on output 73.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 and the RV coil electrode 36 as a common electrode.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with at least one illustrative embodiment, the device 10 supports pacing stimulation therapy within the left ventricle. To this end, the switch 74 may be configured to provide pacing stimulation pulses from the left ventricular pulse generator output 73 to the left ventricular tip electrode 26. In order to preclude the formation of potential blood clots within the left ventricle which may potentially result by virtue of the lead 24 and electrode 26 being within the left ventricle, the device 10, in accordance with one illustrative embodiment, includes a power supply 112 to provide the electrode 126 with a positive voltage with respect to the case 40 and thus the patient. The positive voltage is applied for a time after the electrode 126 is implanted and serves to accelerate a body coating process of the electrode 126. More specifically, this increases the electropositivity of the electrode metal in the blood.

Blood solids have negative charges. A typical platelet has about $2 \times 10^6$ electronic equivalent charges, lymphocytes have a charge of approximately $10.3 \times 10^6$ and erythrocytes have a charge of about $10.3 \times 10^6$. Since these are negative charges, they are naturally attracted to any positive charge. Platinum, for example, in blood generates a positive potential of 0.125 volts on its own. This will tend to attract blood cells. Hence, an additional positive potential applied to the electrode 126 will cause body substances, such as blood cells, plasma and proteins to be deposited on the electrode at an even faster rate. This results in a body coating on the electrode which will serve to repel the formation of blood clots.

The positive voltage is preferably provided to the electrode 126 for a relatively short time, namely between several hours and several days, preferably between about 1 day and about 3 days. The duration of the positive voltage is preferably limited to the time necessary to form the body layer on the electrode. This may be accomplished by monitoring the resistance of the electrode 126. Since the voltage provided is known, the resistance may be monitored by measuring the associated current. To this end, the device 10 further includes a resistance monitor 62. The resistance monitor may, for example, be employed to measure the initial resistance of electrode 126. The initial resistance ($R_O$) maybe on the order of 1 kohm. The positive voltage may then be applied at an initial value of, for example 250 mV, and stepped up to a maximum of, for example, 2 V. During this time, the resistance of the electrode is continuously monitored by the resistance monitor 112. When the resistance reaches a certain value of, for example, $2R_O$ or 2 kohm, the provision of the positive potential is terminated. Thereafter, the electrode may be employed in the desired therapy without further regard to clot formation.

Immediately after the electrode 126 is implanted, and before the positive voltage is a applied to the electrode 126, an anti-clotting agent such as, for example, warfarin, and otherwise know as Cumadin®, may be administered to the patient. This will assure that during the body coating process, a stable and consistent body coating is formed on the electrode without the formation of clots. Once the provision of the positive voltage is terminated, the administering of the anti-clotting agent may be terminated.

Figure 3:
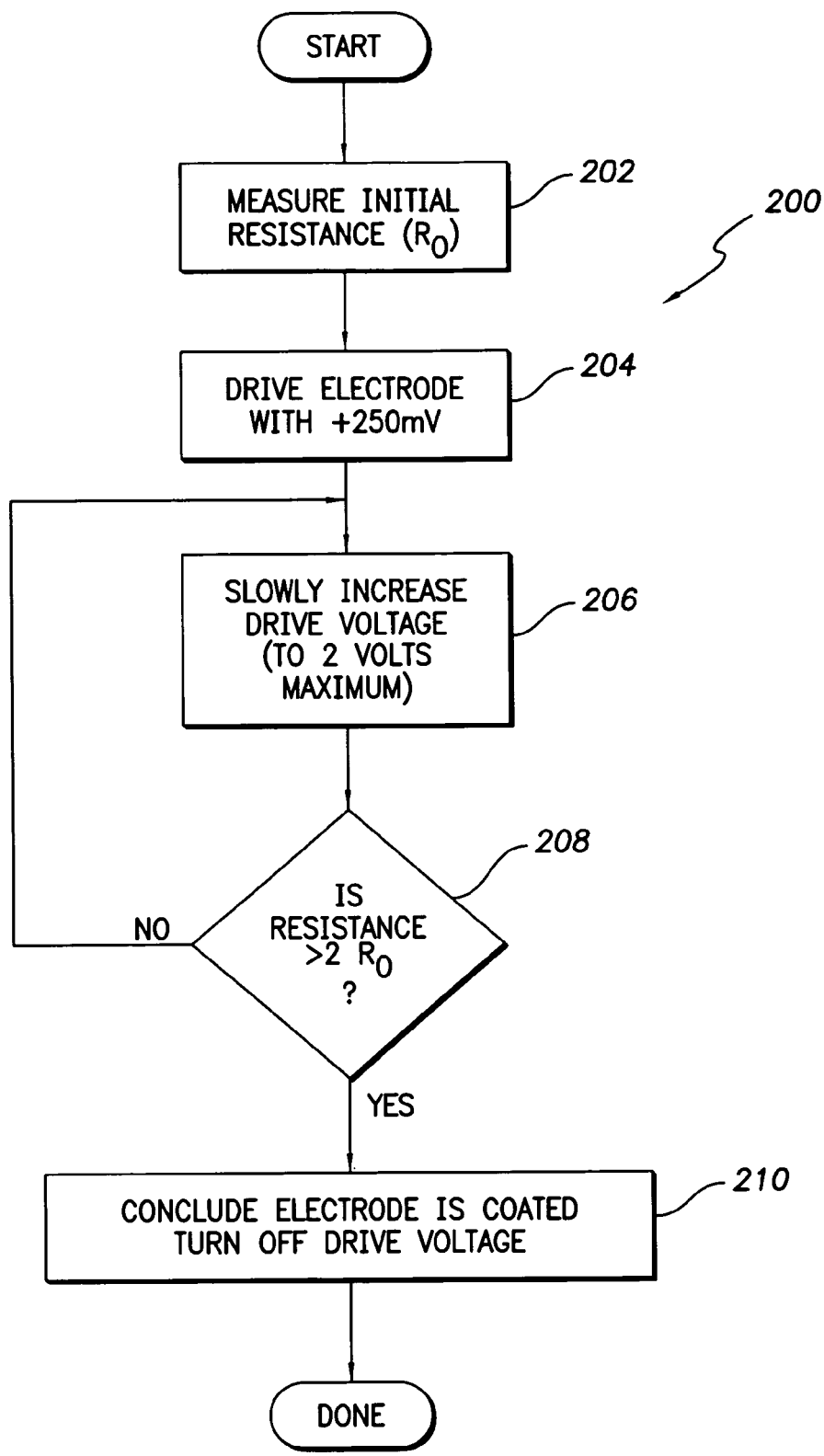
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process begins after the electrode has been implanted and after an anti-clotting agent is given to the patient. The anti-clotting agent is preferably given intravenously.

The process then initiates with activity block 202. Here, the resistance monitor is used to measure the initial resistance ($R_O$) of the electrode. Then, the process advances to activity block 204 where the power supply 112 provides the electrode 126 with a positive voltage having an initial value of, for example, 250 mV.

As represented by activity block 206, the value of the positive voltage is slowly increased to a maximum voltage of, 2 V. As the positive voltage in increased, the resistance of the electrode is continuously monitored. In decision block 208, the measured electrode resistance is compared to a certain value of, for example, twice the initial resistance ($2R_O$). When the electrode resistance reaches $2R_O$, the process advances to activity block 210 where it is concluded that the electrode coating is completed. The positive voltage is then turned off. The patient may then be taken off of the anti-clotting agent and the process is completed. The patient should now be able to receive the desired therapy from the device 10 with a minimal risk of clots being formed on the left ventricular electrode 126.

From the foregoing, it may be seen that the implantable cardiac stimulation device according to the embodiments described herein is capable of providing pacing therapy from within the left ventricle while preventing thrombosis which may otherwise potentially result from such an arrangement. In accordance with the broader aspects of the illustrative embodiments, the pacing electrode within the left ventricular blood pool is provided with a positive voltage of sufficient magnitude and duration to cause a coating of body materials to be deposited on the electrode. This shall thereafter serve to repel and prevent thrombosis formation on the electrode.

While specific embodiments and applications have been described, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system comprising:
at least one implantable lead including at least one stimulation electrode; and
an implantable cardiac stimulation device comprising a pulse generator configured to generate pacing pulses to pace a chamber of a patient's heart, the pulse generator being switchably coupled to the at least one stimulation electrode, a power supply switchably coupled to the at least one stimulation electrode, the power supply being configured to provide the electrode with a voltage as a function of time configured to induce an accelerated body coating process of the electrode, and a switching device configured to first switchably couple the at least one stimulation electrode to the power supply until a body coating layer is formed on the electrode as indicated by a rise in a value of the resistance associated with the electrode above a threshold resistance value and to then switchably couple the at least one stimulation electrode to the pulse generator for application of pacing pulses to the chamber of the patient's heart.

2. The system of claim 1, wherein the power supply is configured to provide the electrode with a positive voltage that is variable as a function of resistance associated with the electrode.

3. The system of claim 2, wherein positive voltage is greater then 250 mV.

4. The system of claim 2, wherein the positive voltage is less than two volts.

5. An implantable cardiac stimulation system comprising:
at least one implantable lead including at least one stimulation electrode;
an implantable cardiac stimulation device comprising a pulse generator switchably coupled to the at least one stimulation electrode and a power supply switchably coupled to the at least one stimulation electrode, the power supply being configured to provide the at least one stimulation electrode with a positive voltage configured to induce an accelerated body coating process of the at least one stimulation electrode;
a resistance monitor that monitors a resistance associated with the electrode and wherein the power supply maintains the positive voltage on the at least one stimulation electrode until the resistance associated with the at least one stimulation electrode reaches a threshold resistance value; and
a switching device that switchably couples the at least one stimulation electrode to the pulse generator in response to the resistance of the least one stimulation electrode reaching the threshold resistance.

6. The system of claim 5, wherein the resistance monitor measures an initial value of the resistance associated with the electrode before the power supply provides the positive voltage and wherein the threshold resistance value is related to the initial resistance associated with the electrode.

7. The system of claim 6, wherein the power supply first provides the voltage at an initial level and increases the voltage level until the resistance associated with the electrode reaches the certain value.

8. The system of claim 1, wherein the at least one implantable lead is arranged to enable implant of the electrode in the left ventricle.

* * * * *